(12) United States Patent
Furlong et al.

(10) Patent No.: US 6,686,202 B2
(45) Date of Patent: Feb. 3, 2004

(54) METHODS FOR DETECTING AND EXTRACTING GOLD

(75) Inventors: Clement E. Furlong, Bainbridge Island, WA (US); Scott Jorgenson-Soelberg, Seattle, WA (US); James B. Clendenning, Seattle, WA (US); Noel W. Kirshenbaum, San Francisco, CA (US); Victor Chevillon, Reno, NV (US); Peter Leon Kowalczyk, Surrey (CA)

(73) Assignees: Placer Dome, Inc., Vancouver (CA); University of Washington, Seattle, WA (US)

( * ) Notice: Subject to any disclaimer, the term of this patent is extended or adjusted under 35 U.S.C. 154(b) by 253 days.

(21) Appl. No.: 09/925,832

(22) Filed: Aug. 8, 2001

(65) Prior Publication Data

US 2003/0124744 A1 Jul. 3, 2003

(51) Int. Cl.[7] .................. G01N 33/24; G01N 33/20
(52) U.S. Cl. .............. 436/26; 436/80; 436/86; 436/172; 436/525; 502/403
(58) Field of Search ............ 436/26, 80, 86, 436/172, 525; 502/403

(56) References Cited

U.S. PATENT DOCUMENTS

| 4,722,892 A | 2/1988 | Meares et al. |
| 4,769,223 A | 9/1988 | Volensky et al. |
| 4,789,481 A | 12/1988 | Brierly et al. |
| 5,354,658 A | 10/1994 | Wright |
| 5,378,437 A | 1/1995 | Kleid et al. |
| 5,503,987 A | 4/1996 | Wagner et al. |
| 5,567,316 A | 10/1996 | Spears et al. |
| 6,033,878 A | 3/2000 | Matsunaga |

FOREIGN PATENT DOCUMENTS

WO    WO 97/14818    4/1997

OTHER PUBLICATIONS

Al–Asheh & Duvnjak (1996) *J. Hazardous Mat.* 48:83–93.
Brown (1997) *Nat. Biotech.* 15:269–72.
Bontideau et al. (1997) *Anal. Chem.* 70:1842–1848.
Ishikawa & Suyama (1998) *App. Biochem. and Biotech* 70–72:719–728.
Niu & Volesky (2000) *J. Chem. Tech. and Biotech.* 75:436–442.
Woodbury et al. (1998) *Biosensors and Bioelectronics* 13:1117–1126.

*Primary Examiner*—Jill Warden
*Assistant Examiner*—Monique T. Cole
(74) *Attorney, Agent, or Firm*—Swanson & Bratschun, LLC

(57) ABSTRACT

Methods for detecting gold and quantitating gold in ore samples utilizing a gold-specific protein are provided, including methods for multiple sample handling. Also provided are methods for extracting gold from mineral suspensions utilizing a magnetic mineral binding reagent and gold-specific protein, or hydrophobic reagent and gold-specific protein in conjunction with a flotation reagent.

11 Claims, 5 Drawing Sheets

METHODS FOR DETECTING AND EXTRACTING GOLD

FIELD OF THE INVENTION

This invention relates generally to the use of non-naturally occurring specific gold-binding proteins or peptides for use in analytic, exploration or recovery methods in the gold mining industry.

BACKGROUND OF THE INVENTION

Gold is one of the rarest precious metals on earth. It occurs naturally as the reduced metal (Au°) or associated with quartz or pyrites as telluride ($AuTe_2$), petzite $(AuAg)_2Te$ or sylvanite $(AuAg)Te_2$. The electronics and space industries use gold's properties of electrical conductivity and heat reflection. Gold has applications in radar equipment, home computers, satellites and space exploration. Gold is also used in considerable quantities in the form of gold leaf (having a thickness of less than 0.2 $\mu$m) for sign writing and book binding lettering. Gold film has been used in glass windows to reflect heat. Liquid gold is a suspension of very finely divided gold particles in vegetable oil that is used in the decoration of china articles. Gold salts are used for toning in photography, and in coloring glass.

Most frequently gold in nature is dispersed in low concentration throughout large volumes of material, usually rock. Gold deposits occur in belts across the earth's crust in various forms: placers or quartz veins in sedimentary or indigenous formation, blanket or pebble beds or conglomerates, or as base metal ore associations. Gold occurs in ore bodies described as lodes or veins, replacement deposits, contact (skarn) deposits, volcanogenic deposits, deposits associated with intrusive activity (such as 'porphyry' systems and breccia pipes) and deposits associated with ferruginous sediments (banded iron formations) and cherts. Gold bearing veins are found in rocks of all compositions and geologic ages, deposited in cavities and associated with rocks such as slates or schists. Lode deposits consist of gold particles contained in quartz veins or country rock. Lode deposits usually are mined in deep underground mines using a variety of methods, although sometimes lode deposits are surface mined. The blanket or reef-type deposits are deposits in which the gold exists in quartz conglomerates. Disseminated gold deposits have three identifying characteristics. The gold mineralization is fairly evenly distributed throughout the deposit rather than being concentrated in veins (as in lode deposits) or in pay-streaks (as in placer deposits); the deposits consist of in place materials rather than transported materials; and the disseminated deposits are less flat. Generally, these types of deposits are mined using surface mining techniques.

Gold also exists in secondary ore deposits. All rock outcrops exposed at the surface of the earth are subjected to the natural elements of weathering and erosion, causing eventual breakdown of rock into fragments which are carried away by wind, water or ice. The fragments are then redeposited in river systems, lakes or in the sea. During the erosive cycle, the heavier and more durable gold is concentrated into rich deposits, even though the original rock may have contained low values. Residual deposits of gold are found close to the gold bearing outcrop after the other rock fragments have weathered and been carried away. Eluvial deposits are formed when gold or gold bearing rock fragments have been transported short distances from their source (generally by gravity) and have been concentrated within the soil horizon. Alluvial deposits are formed by the concentration of gold particles within stream systems, under the action of running water. Beach placers, where gold is concentrated in beach sands by wave action, are a type of alluvial deposit. Leads are former stream courses, containing gold, where barren sands have covered the original passage of the stream. Deep leads are gold deposits in former stream beds which have been covered with basaltic lava. Nuggets are formed, either as rich fragments of primary deposits which have been transported and deposited in a sedimentary environment, or a chemical accretion of small gold particles into larger fragments. Some nuggets may have formed through the chemical action of host soils or sediments on a gold solution. Placer deposits are flat-laying deposits composed of unconsolidated materials, such as gravel and sands, in which the gold particles occur as free particles ranging in size from nuggets to fine flakes. They are the result of erosion and transport of rock. Placer deposits most commonly are mined using water based surface methods, including hydraulic methods, dredging and open pit mining. These deposits usually are not mined in underground operations.

Methods for recovering gold from its ores (termed "beneficiation methods") are extremely expensive and labor and heavy machinery intensive. Gold is one of the least reactive metals on earth. It does not combine with oxygen or with nearly any other chemicals, no matter how corrosive. Some gold ores are free milling and allow the separation of coarse gold using methods that depend on the high specific gravity of gold. All other commonly used methods depend on the use of cyanide which is highly toxic, hazardous to the environment and difficult to remove. Basically, the first step in all methods is to subject the ore to cyanide leaching followed by a gold recovery process. The three known methods for extracting gold from the cyanide leach solution are the "Merrill-Crowe" or zinc dust precipitation process, the carbon-in pulp process, and the carbon in-leach process. Other gold recovery processes use gravity methods to extract the high proportion of free gold and flotation-roasting leaching to extract the remaining gold.

Cyanide and cyanide by-products from cyanide leaching operations are responsible for several environmental impacts, including air and water pollution and solid waste disposal contamination. Free cyanide and various cyanide complexes are the by products of current leaching methods. Although cyanide will degrade, for example in a surface stream exposed to ultraviolet light, aeration and complexing with various chemicals present in the stream water, in-stream degradation is a wholly unsatisfactory approach to removing cyanide from the environment. Cyanide solutions are often kept in open ponds and frequently birds or other animals are exposed and killed by the toxic material.

Air pollution with cyanide also is an unavoidable result of prior art methods for heap-leaching of gold. Cyanide solutions are sprayed onto the heaps, the cyanide drifts and contaminates the surrounding environment. As is the case with cyanide released into water, eventually the cyanide is degraded by ultraviolet light, but not until after it has adversely affected the environment. The EPA directs considerable efforts and expense in regulating cyanide releases into the air and water. Chronic cyanide toxicity due to long-term exposures to low levels is also a health factor to be considered, and the effects such exposures are not presently well known. For these reasons there has been a long standing need for gold mining processes which do not pollute the environment with cyanide and cyanide byproducts.

Gold recovery from secondary sources such as electronic scrap and waste electroplating solutions, as well as recovery from primary sources such as leach solutions is also an important technology. Various processes such as carbon adsorption, ion exchange, membrane separation, precipitation, and solvent extraction have been used for isolation of metal ions, including gold.

Recently, methods for the utilization of naturally occurring proteins or biologic materials in analytic or gold recovery, including microbial biomass, as an adsorbent for metals have been studied. Bontideau et al., *Anal. Chem.* 70:1842–1848 (1997) is a physical chemical study of the two-dimensional binding properties between a naturally occurring protein and a gold substrate. The arrangement and enzymatic activity of a myosin sub-fragment were characterized with special focus on the direct attachment of the thiol groups of cysteines in the protein to the gold substrate.

The current process for gold recovery includes treatment with cyanide to form a gold cyanide complex. U.S. Pat. No. 5,378,437 of Kleid et al teaches the use of cyanide-secreting microorganisms that also absorb the cyanide gold complex once formed.

A large body of research exists that describes, as an alternative to cyanide, the utilization of biomass to recover gold from aqueous solution or suspension. U.S. Pat. No. 4,789,481 of Brierley describes an improvement over the basic biomass extraction process whereby the biomass—in this case *Bacillus subtilis*—is treated with a caustic solution prior to use. U.S. Pat. No. 4,769,223 of Volesky et al., is directed to the biomass process where the biomass is derived from the growth of the marine algae of the genus Sargassum. U.S. Pat. No. 5,567,316 of Spears et al., describes a process for recovering metals from solutions using an immobilized metalloprotein material. There is no suggestion that this process would be useful for the recovery or detection of gold.

Different processes of enrichment of gold-containing ore are known in the art. Flotation is one of the most widely used of these processes. In this method, separation is accomplished by treating ground ore with chemical reagents that cause one fraction to sink to the bottom of a body of water and the other fraction to adhere to air bubbles and rise to the top. The flotation process was developed on a commercial scale early in the 20th century to remove very fine mineral particles that formerly had gone to waste in gravity concentration plants. Most kinds of minerals require coating with a water repellent to make them float. By coating the minerals with small amounts of chemicals or oils, finely ground particles of the minerals remain unwetted and will thus adhere to air bubbles. The mineral particles are coated by agitating a pulp of ore, water, and suitable chemicals; the latter bind to the surface of the mineral particles and make them hydrophobic. The unwetted particles adhere to air bubbles and are carried to the upper surface of the pulp, where they enter the froth; the froth containing these particles can then be removed. Unwanted minerals that naturally resist wetting may be treated so that their surfaces will be wetted and they will sink. Processing the flotation concentrate in order to recover gold is simpler and cheaper than treatment of total ore stock. Current flotation technology, however, still does not recover all of the gold that is present, especially the gold in finely-dispersed ore. At least one attempt has been made to improve the flotation process using a microorganism culture. Cormack, et al., Gold Extraction Process for Bioflotation, WO 97/14818. In this method, a microorganism culture is introduced into flotation tails and the mixture is agitated.

Most reported research in the area of protein/gold interactions describes the adsorption of gold or other metals by proteins in a non-specific fashion. Ishikawa & Suyama, Recovery and Refining of Au by Gold-Cyanide Ion Biosorption Using Animal Fibrous Proteins, App. Biochem. and Biotech., 1998, 70–72:719–728, is typical. Animal fibrous proteins which were insoluble and stable in water, such as chicken feather protein and hen eggshell membrane, adsorbed gold in a non-specific fashion. In this reference, eggshell membrane was utilized in a column and was able to remove very low concentrations of gold from aqueous solution. Another typical reference which provides generic disclosure of protein/gold or protein/metal ion interactions is Alasheh & Duvnjak, Adsorption of Copper by Canola Meal, J. Hazardous Mat., 1996, 48:83–93. Niu & Volesky, Gold-cyanide Biosorption with L-cysteine, J. Chem. Tech, and Biotech., 2000, 75:436–442, describe the chelation properties of a particular amino acid. In this reference, biomass was "loaded" with L-cysteine by contacting dried, protonated biomass with a solution of L-cysteine, and resulted in the ability of the biomass to adsorb higher concentrations of gold-cyanide. The authors postulate that the enhanced binding probably results from binding the gold-cyanide complex to the cysteine $NH_3^+$, while the cysteine $COO^-$ binds to positive charges on the biomass.

Brown, Nat. *Biotech.* 199715:269–72, herein incorporated by reference in its entirety, has engineered a fusion protein including *E. coli* alkaline phosphatase and an engineered gold binding peptide domain. The identification of the gold binding domain involved fusion of a combinatorial library of peptide repeat sequences to an outer membrane protein of *E. coli*. Cells were selected for their ability to attach to Au beads. The Au-binding domains that appeared to have high specificity and affinity for Au were then engineered as fusion peptides to the *E. coli* enzyme alkaline phosphatase (referred to as gold-binding protein or GBP). The attachment of the Au-binding domain to the enzyme provided a convenient means to follow (quantify) binding to Au surfaces. With respect to applications of this novel material, the article was principally concerned with studies on metal protein interactions. Woodbury et al., *Biosensors and Bioelectronies*, 13:1117–1126 (1998), is directed to the general application of the gold-binding peptides suggested by Brown. The biosensors described in the Woodbury et al. reference utilized the gold-binding peptides to attach recognition elements to the gold sensor surface. Detection of binding events to the recognition element is performed by surface plasmon resonance (SPR). Although the gold-binding peptide and its affinity to gold is an element of this article, the gold-binding peptides affinity to gold is not exploited for analytic or gold recovery applications.

SUMMARY OF THE INVENTION

The present invention provides methods for detecting gold in ore samples, using a gold-specific protein for binding to the sample. Such methods may be qualitative or quantitative. In one embodiment, the method is a direct-binding method. In another embodiment, the non-specifically bound gold-binding protein is proteolyzed and detected. The methods have been adapted for a high-throughput format, such as a multiwell plate.

The present invention also provides methods for extracting gold from a mineral suspension containing gold and magnetite, using a magnetite-binding gold-specific protein to form a magnetic complex and extracting gold using a magnetic field.

The present invention also provides flotation methods for extracting gold from a mineral suspension, using a gold-specific protein with a hydrophobic tail as a flotation reagent.

DETAILED DESCRIPTION OF THE PREFERRED EMBODIMENTS

Figure 1:
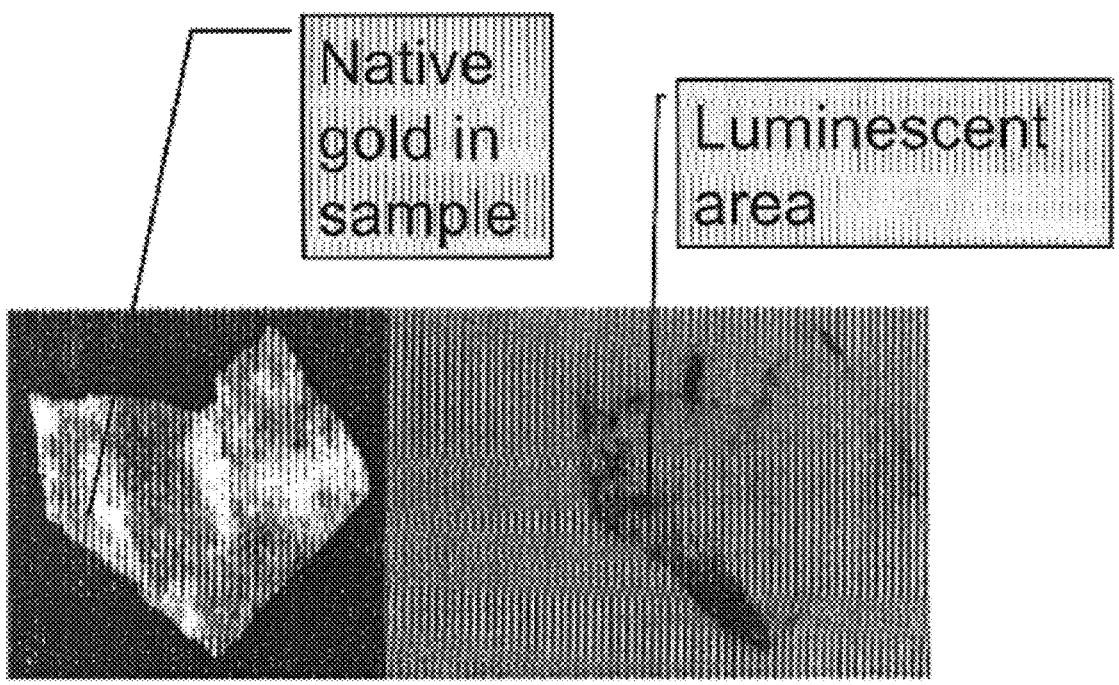
FIG. 1 shows localization of gold with the "rock blot".

The present invention is directed to the use of non-naturally occurring specific gold-binding proteins or peptides in all areas of the mining industry including prospecting, exploration and development, actual mining, such as surface mining and underground mining, sustainable mining, sampling, concentration, beneficiation, and environmental remediation. In particular embodiments of the invention, uses include locating gold in field samples with intact or proteolyzed proteins, recovering gold with a magnetic gold-binding protein, and recovering gold via flotation with a gold-binding protein suitable as a flotation reagent. A magnetic gold-binding protein can be generated by techniques known to those skilled in the art, for example, by derivatizing magnetic beads with the gold-binding protein. Further embodiments include recovering gold using chemotactically sensitive microbes producing gold-binding protein and methods for determining the source of metal ions in streams, rivers, and drainage basins by using immobilized gold-binding proteins in these locations.

The gold binding proteins of the present invention are proteins that have a high specificity and affinity for gold. The preferred gold-binding proteins of the present invention are those identified as described by the methods in Brown, *Nat. Biotech.* 199715:269–72, and most preferably are the proteins set forth in Brown. However, the present invention is not limited to such proteins and specifically includes any gold-specific binding protein defined as a having high specificity and affinity for gold, obtained by any method. For example, the present invention includes monoclonal antibodies specific for metal ions including gold ions that are described in U.S. Pat. No. 5,503,987 to Wagner, et al, incorporated by reference herein in its entirety. In fact the present invention also extends to any other gold-specific binding, non-naturally occurring ligand to gold, be it a protein, polypeptide, peptide, protein fragment, oligonucleotide, carbohydrate, antibody, chelating agent, magnetic agent, hydrophobic agent, or combination thereof, that can be used in the methods of the present invention. As an example, in one embodiment of the invention, gold-binding protein is associated with magnetic beads to generate a magnetic gold-binding protein reagent. In another embodiments, a gold-binding protein is modified with hydrophobic tails to generate a hydrophobic gold-binding protein suitable as a flotation reagent. Additionally, methods of the present invention include the use of other proteins, such as the monoclonal antibodies specific for metal chelates as are described in Meares, et al., U.S. Pat. No. 4,722,892, incorporated by reference herein in its entirety.

I. Field System for Mineral Exploration ("Rock Blot")

The present invention is directed toward a method for locating gold in field samples with a protein having high specificity and affinity for gold. As used herein, Au-specific protein or gold-specific protein refers to a protein having high specificity and affinity for gold. In one embodiment, the method is useful in characterizing the distribution of gold within deposits. Samples are first treated with blocking reagents well known in the art (e.g., protein, detergents) to prevent the Au-specific protein from binding to sites that have general affinity for protein. The sample is then exposed to an Au-specific protein. In a preferred embodiment, the Au-specific protein is alkaline phosphatase (AP) engineered with a Au-binding domain, or $AP_{Au}$. $AP_{Au}$ is also referred to as GBP (gold-binding protein). The sample is washed and the location of the bound $AP_{Au}$ is determined by using a detectable substrate for alkaline phosphatase, for example, using standard ELISA techniques. In a preferred embodiment, the substrate is a luminescent substrate, detected by exposing overlaid film to light generated by the $AP_{Au}$ and a substrate that generates light when hydrolyzed by $AP_{Au}$. Other suitable substrates are well-known to those skilled in the art. Examples of suitable substrates include 5-bromo-4-chloro-3 indolyl phosphate (BCIP), utilized in U.S. Pat. No. 5,354,658, and p-nitrophenyl phosphate, a water-soluble substrate. Indirect detection methods are also useful in the present invention, for example, a sandwich ELISA.

FIG. 1 shows the results of a typical assay. This assay has been termed a "rock blot" by the inventors. A rock section with visible Au was provided to serve as both a sample and control. The exposed areas of the film clearly line up over the Au deposits in the sample. The details of the protocol are included in Example 1.

II. High-throughput Gold Detection Protocol

The present invention also provides methods to quantify the surface area of Au exposed on ore samples in a high-throughput assay. The basic method is similar to the "rock blot," but incorporates additional steps to reduce background signal generated by the reaction of the mineral matrix with the preferred luminescent substrate. In this assay, GBP was allowed to bind to a milled ore sample. The AP domains bound to the areas of the ore matrix that bound protein nonspecifically, while the Au-binding domain more specifically binds Au. Following this initial binding, the samples were treated briefly with a proteolytic agent cleaving the protein, and releasing into the supernatant any GBP bound only through its Au-binding domain. As used herein, proteolytic agent refers to a reagent that is capable of chemically or otherwise splitting proteins into smaller peptide fractions and amino acids. Proteolytic agents useful in the present invention include proteolytic enzymes such as proteases, peptidases, and proteinases. Examples of proteolytic enzymes are Lys C, Arg C, Asp N, Glu C, trypsin, chymotrypsin, pepsin, thermolysin, and proteinase K Nonenzymatic proteolytic agents include cyanogen bromide (CNBr) and formic acid (COOH). In a preferred embodiment, the proteolytic agent is trypsin. The alkaline phosphatase cleaved from the Au-binding domain and released into the supernatant was removed from the matrix-containing reaction and was quantified by measuring the activity of the alkaline phosphatase. A very sensitive assay for alkaline phosphatase involves cleavage of the substrate LUMI-PHOS® Plus (Lumigen, Inc., Southfield, Mich.) to produce light, which is quantified in a luminometer.

Experiments with milled ore samples containing high or low levels of Au led to the development of incubation and wash conditions that differentiated high Au containing samples from samples with low levels of Au.

The need to examine high numbers of samples required the development of a high-throughput analysis (96 well plate assay). "Saw chips" from a core-split were used to compare the plate assay with a standard fire assays of one-half of the core.

The fire assay is a potentially highly precise and accurate method for the total determination of Au and other precious metals in samples. It is typically used on ore-grade samples. The fusion, or "melt" is done in a furnace at high temperatures; hence the term "fire" assay. Samples are mixed with fluxes including lead-oxide, fused at 1050° C., cupeled to recover a dore bead, nitric acid parted to separate the precious metal then analyzed by either gravimetric, atomic absorption, or other analytical method. The fire assay does have drawbacks, however. First, the sample size is relatively large, requiring about one "assay ton" of pulverized sample, i.e. 29.84 grams of material. Second, certain types of ore contain elements that may interfere with the result. A good fire assayer knows how to modify the composition of the flux to avoid these problems, thus highly skilled and experienced assayers are necessary to achieve high quality results in a fire assay for gold.

Figure 2:
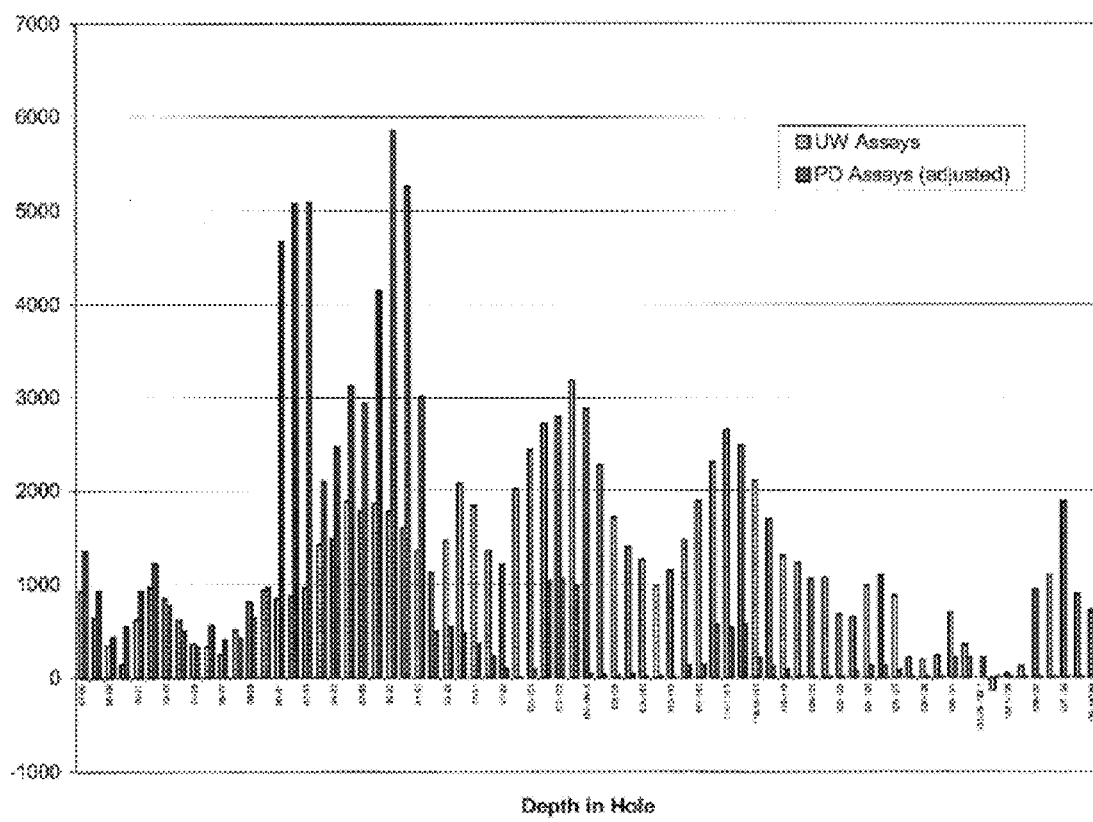
FIG. 2 shows a comparison of UW 96 well assay with fire assay using core split chips.

FIG. 2 shows the results of a comparison of the fire assay with the GBP assay (average of three replicates) using a three point sample average smoothing. Overall, there was an excellent agreement between the results of the fire assay and the plate assay, particularly for samples from the upper region of the core. Application of the 96-well plate assay shows that replicate assays had small variance between replicates and differentiates between milled samples with high or low Au content.

Figure 3A:
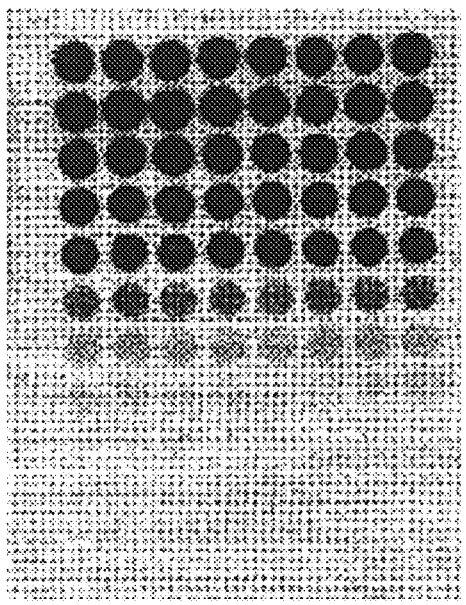
FIG. 3A shows a film analysis of 96 well plate assay where the exposure to film was a 10 second exposure.
Figure 3B:
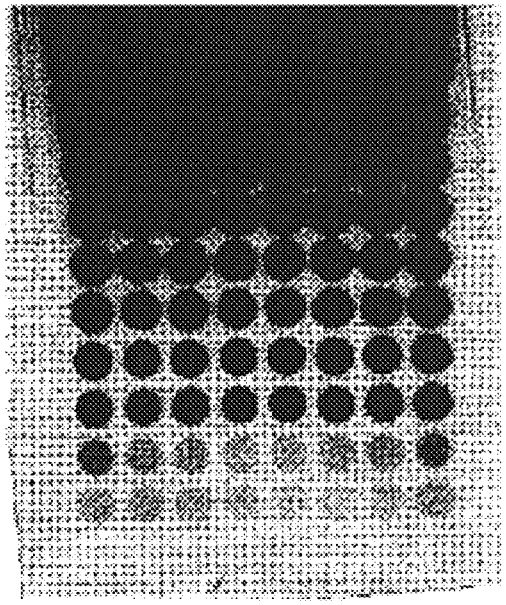
FIG. 3B shows a film analysis of the same 96 well plate assay where the exposure to film was a 10 minute exposure.

In another embodiment, suitable for use in the field, the 96 well plate is exposed to film, as it would be much more convenient to analyze film in the field than carry out luminometer determinations. A POLAROID® film result can be scanned with a simple PC scanner device and the results quantified. Normal film can be scanned by a simple densitometer. In another embodiment, normal film or X-ray film is used, and, once exposed and developed, is taped the bottom of a 96 well plate and analyzed in a plate reader at 500 nM. The results of a sample quantitation are shown in Table 1 below and in FIG. 3. In the sample plate, eight replicate well sets were used, and enzyme concentration was reduced by one-half for twelve steps. FIG. 3A shows a film exposed for 10 seconds, and FIG. 3B shows the same experiment with a film exposure of 10 minutes. These procedures are detailed in Example 2.

TABLE 1

Absorbance Values from Molecular Devices Plate Reader for 96-Well Plate (10 second exposure)

|   | 1 | 2 | 3 | 4 | 5 | 6 | 7 | 8 | 9 | 10 | 11 | 12 |
|---|---|---|---|---|---|---|---|---|---|---|---|---|
| A | 2.105 | 2.538 | 2.802 | 1.202 | 0.708 | 0.409 | 0.272 | 0.218 | 0.206 | 0.202 | 0.193 | 0.190 |
| B | 1.306 | 2.615 | 2.226 | 1.204 | 0.713 | 0.390 | 0.261 | 0.206 | .202 | .194 | 0.195 | 0.189 |
| C | 1.893 | 2.737 | 2.261 | 1.326 | .767 | 0.412 | 0.272 | 0.209 | 0.197 | 0.192 | 0.190 | 0.191 |
| D | 0.291 | 2.618 | 2.164 | 1.237 | 0.703 | 0.362 | 0.249 | 0.199 | 0.193 | 0.184 | 0.186 | 0.192 |
| E | 2.107 | 2.571 | 2.254 | 1.307 | 0.722 | 0.399 | 0.264 | 0.214 | 0.195 | 0.182 | 0.186 | 0.187 |
| F | 1.674 | 2.632 | 2.196 | 1.257 | 0.700 | 0.390 | 0.257 | 0.203 | 0.2 | 0.188 | 0.188 | 0.179 |
| G | 2.036 | 2.552 | 2.118 | 1.173 | 0.729 | 0.422 | 0.270 | 0.209 | 0.195 | 0.190 | 0.187 | 0.181 |
| H | 2.209 | 2.572 | 2.214 | 1.333 | 0.728 | 0.401 | 0.278 | 0.222 | 0.193 | 0.188 | 0.183 | 0.182 |

(10 minute exposure)

|   | 1 | 2 | 3 | 4 | 5 | 6 | 7 | 8 | 9 | 10 | 11 | 12 |
|---|---|---|---|---|---|---|---|---|---|---|---|---|
| A | 3.858 | 3.846 | 3.724 | 3.620 | 3.651 | 3.505 | 3.332 | 2.850 | 2.120 | 1.119 | 0.469 | 0.279 |
| B | 3.527 | 3.560 | 3.575 | 3.494 | 3.416 | 3.374 | 3.186 | 2.614 | 1.794 | 0.915 | 0.351 | 0.255 |
| C | 3.477 | 3.522 | 3.457 | 3.495 | 3.376 | 3.408 | 3.185 | 2.708 | 1.709 | 0.858 | 0.307 | 0.242 |
| D | 3.669 | 3.648 | 3.592 | 3.595 | 3.527 | 3.340 | 3.219 | 2.530 | 1.560 | 0.725 | 0.309 | 0.237 |
| E | 3.824 | 3.754 | 3.702 | 3.712 | 3.641 | 3.520 | 3.299 | 2.889 | 1.603 | 0.773 | 0.323 | 0.232 |
| F | 3.719 | 3.826 | 3.798 | 3.693 | 3.652 | 3.516 | 3.378 | 2.765 | 1.898 | 0.943 | 0.387 | 0.258 |
| G | 3.661 | 3.732 | 3.651 | 3.602 | 3.554 | 3.476 | 3.37 | 2.846 | 1.657 | 1.024 | 0.384 | 0.275 |
| H | 3.791 | 3.823 | 3.841 | 3.880 | 3.733 | 3.653 | 3.414 | 3.065 | 2.066 | 1.048 | 0.521 | 0.307 |

Figure 4A:
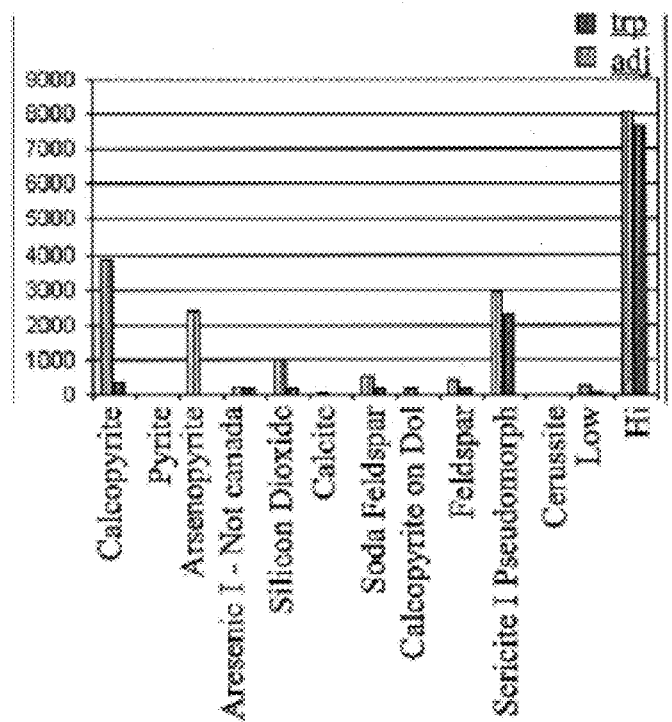
FIG. 4A displays the results of each 96 well plate assay specificity sample along with a high and low ore standard. The "trp" and "adj" labels represent the signal from the trypsinized sample and then a background adjusted result.
Figure 4B:
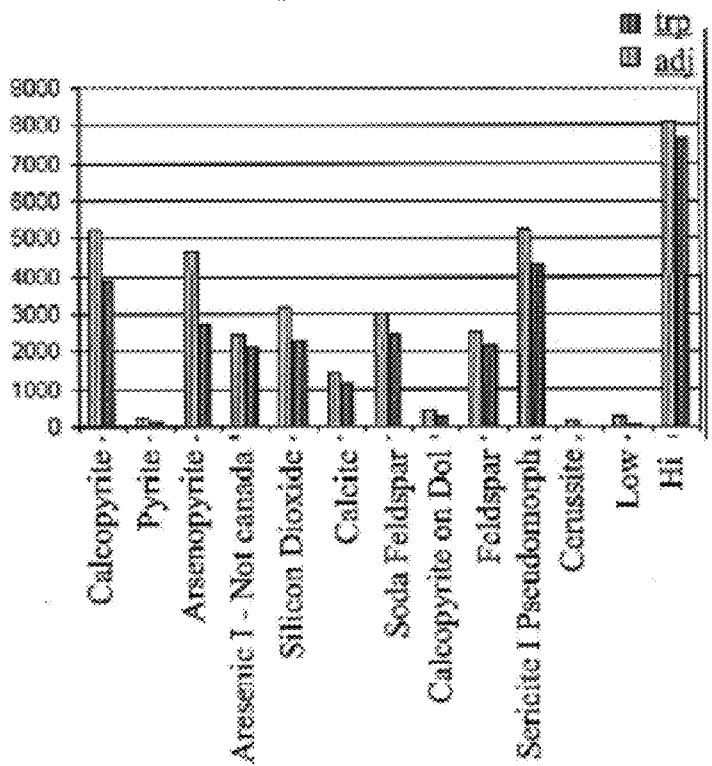
FIG. 4B displays the results of a 50/50 mix of the specificity sample and the high (7.59 g/t) ore standard.
Figure 5:
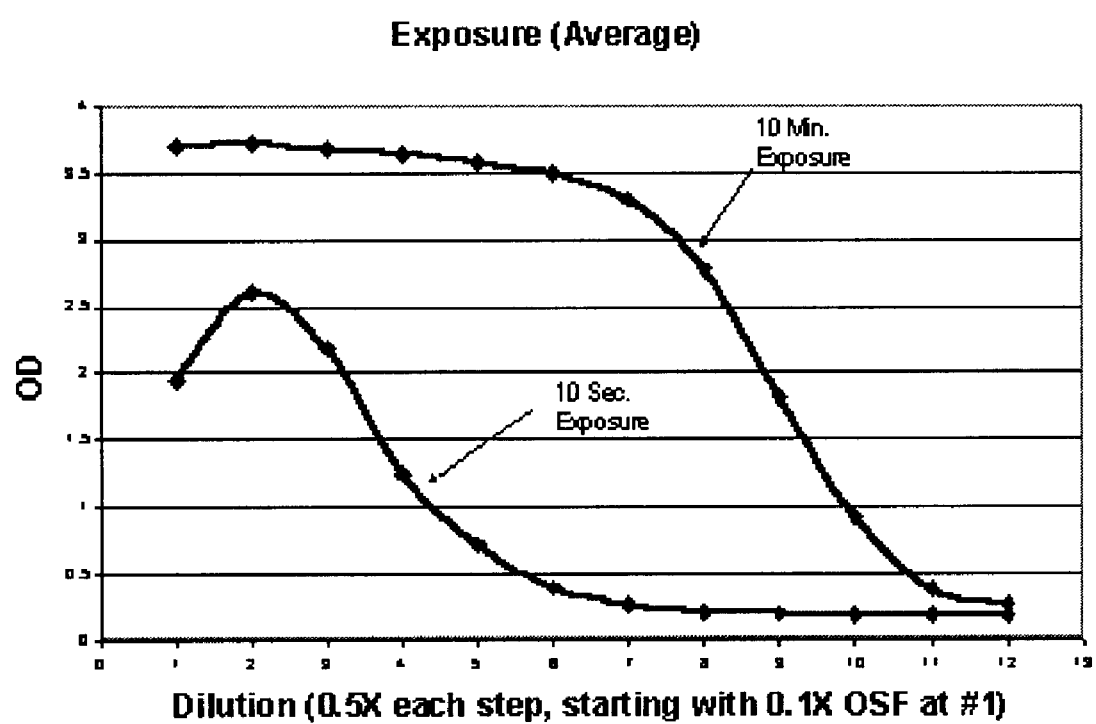
FIG. 5 show the results of the film analysis in a graphical form.

A number of different mineral samples were tested using the plate assay to determine the levels of nonspecific binding. Table 2 contains the raw data. FIG. 4 depicts the averages listed on the table in graphical form. FIG. 4A displays the results of each specificity sample along with a high and low ore standard. The "trp" and "adj" labels represent the signal from the trypsinized sample and then a background adjusted result. FIG. 4B displays the results of a 50/50 mix of the specificity sample and the high (7.59 g/t) ore standard.

TABLE 2

Raw data from specificity assay:

| Sample only | trp | | ave | trp- | | ave | adjusted |
|---|---|---|---|---|---|---|---|
| Calcopyrite | 3954 | 3710 | 3832 | 3538 | 3409 | 3474 | 359 |
| Pyrite | 0.75 | 0.91 | 1 | 1.53 | 1.48 | 2 | −1 |
| Arsenopyrite | 2402 | 2444 | 2423 | 2900 | 2727 | 2814 | −391 |
| Aresenic I-Not canada | 229 | 262 | 246 | 31.3 | 69.9 | 51 | 195 |
| Silicon Dioxide | 1068 | 913 | 991 | 1078 | 596 | 837 | 154 |
| Calcite | 34.6 | 96 | 65 | 157 | 165 | 161 | −95 |
| Soda Feldspar | 441 | 582 | 511 | 381 | 280 | 330 | 181 |
| Calcopyrite on Dol | 162 | 163 | 162 | 149 | 192 | 170 | −8 |
| Feldspar | 380 | 386 | 383 | 245 | 203 | 224 | 160 |
| Sericite I Pseudomorph | 3153 | 2680 | 2917 | 665 | 661 | 663 | 2254 |
| Cerussite | 0.62 | 12 | 6 | 5.36 | 5.54 | 5 | 1 |
| Low | 286 | 224 | 255 | 155 | 253 | 204 | 52 |
| Hi | 7990 | 8104 | 8047 | 565 | 206 | 385 | 7662 |
| Sample spiked with 50% high Au ore | trp | | ave | trp- | | ave | adjusted |
| Calcopyrite | 5229 | 5244 | 5237 | 1279 | 1402 | 1341 | 3896 |
| Pyrite | 265 | 132 | 198 | 110 | 80.3 | 95 | 103 |
| Arsenopyrite | 4315 | 4966 | 4641 | 2308 | 1514 | 1911 | 2730 |
| Aresenic I-Not canada | 2388 | 2473 | 2431 | 320 | 302 | 311 | 2119 |
| Silicon Dioxide | 3285 | 3040 | 3163 | 673 | 1070 | 872 | 2291 |
| Calcite | 1496 | 1323 | 1410 | 195 | 320 | 258 | 1152 |
| Soda Feldspar | 3082 | 2940 | 3011 | 610 | 543 | 576 | 2435 |
| Calcopyrite on Dol | 321 | 601 | 461 | 330 | 76.3 | 203 | 258 |
| Feldspar | 2406 | 2613 | 2510 | 414 | 206 | 310 | 2199 |
| Sericite I Pseudomorph | 4992 | 5528 | 5260 | 985 | 965 | 975 | 4285 |
| Cerussite | 135 | 148 | 142 | 166 | 132 | 149 | −7 |
| Low | 286 | 224 | 255 | 155 | 253 | 204 | 52 |
| Hi | 7990 | 8104 | 8047 | 565 | 206 | 385 | 7662 |

III. Gold Recovery System (Magnetic Separation).

It is a further object of this invention to provide a method for the recovery of gold from a liquid containing a magnetic mineral. In this method, a magnetic mineral binding reagent including a gold-specific protein is added to the sample to form a complex of magnetic mineral and gold. When a magnetic field is applied to the sample, the complex is removed from the rest of the solution, allowing the recovery of the gold. The magnetic mineral binding reagent and the gold-specific protein may be associated by covalent or non-covalent means.

In a preferred embodiment, the liquid is a slurry containing magnetite and fine gold. Magnetite, sometimes called magnetic iron, is an oxide of iron ($Fe_3O_4$) occurring in isometric crystals, also massive, of a black color and metallic luster. It is readily attracted by a magnet and sometimes possesses polarity, in which case it is called lodestone. As there is often a significant quantity of magnetite in the gold-processing stream, and a substantial amount of fine Au is lost during processing, this method provides a solution to the problem of this lost Au. In the case of ores with low magnetite, the method may be used upon addition of magnetite to the slurry.

In order to test the concept, Au beads (≈3 μm diameter) were coated with GBP and rabbit anti-alkaline phosphatase antibodies. The coated beads were in turn bound to magnetic beads coated with goat anti-rabbit antibodies. The complex was readily pulled to the wall of a micro-centrifuge tube in the presence of a magnetic field, while the controls stayed suspended and gradually settled to the bottom of the tube.

In one embodiment, a reagent with both gold-and magnetite-binding domains is added to bind gold and the natural magnetite, then the complex is extracted using magnetic means.

In another embodiment, a GBP bound to a magnetic particle is used. Methods for generating protein-bound magnetic particles are described in U.S. Pat. No. 6,033,878, herein incorporated by reference in its entirety.

In another embodiment, magnetic mineral binding reagent is a microbial cell expressing two different metal binding domains on its surface, one for gold and one for magnetite. In another embodiment, different cells, each expressing a different domain can be cross-linked to provide the reagent. Another way to achieve this aim is to make a fusion protein with both binding domains.

IV. Gold Flotation

In another embodiment, the present invention provides a gold flotation reagent. In one embodiment, the gold flotation reagent is a hydrophobic reagent comprising a gold-specific protein. As used herein, hydrophobic moiety refers to a substance that repels or is insoluble in water. The hydrophobic moiety may be any hydrophobic moiety. Simple hydrophobic moieties such as a $C_5$ tail are suitable, as well as larger and more complex hydrophobic groups. Suitable hydrophobic groups include those derived from the organic acids butanoic acid, maleic acid, valeric acid, hexanoic acid, phenolic acid, cyclopentanecarboxylic acid, benzoic acid, and the like. Other suitable hyrdrophobic moieties include protein domains consisting of the hydrophobic amino acids alanine, valine, leucine, isoleucine, phenylalanine, tyrosine, and tryptophan. Naturally-occurring proteins with such hydrophobic tails or domains are known to those skilled in the art, as are methods for the creation of fusion proteins with such hydrophobic domains.

The ability of a gold-specific protein to act as a flotation reagent is evidenced by an experiment with a modified gold-specific protein. GBP was modified with valeric anhydride to create a GPB with $C_5$ hydrophobic tails ($C_5$-GPB). After binding to gold particles, valeric anhydride was added to acylate the bound GBP. Mineral oil was then added. After mixing, followed by separation of the oil and water layers, it was found that the $C_5$-GBP bound to gold resided at the oil water interface. The experiment shows that gold bound to $C_5$-GBP possesses sufficient hydrophobic character to be used in a flotation process.

V. Use of Microbes to Extract and Deliver Metals from Ores.

In another embodiment, the present invention provides a method to recover very small gold from crushed samples or from samples with free particles of sub micron to micron size gold. In one embodiment, the method utilizes microbial strains that express gold binding domains on their surfaces. The cells are directed to deliver the bound Au to the destination by taking advantage of their ability to swim up a concentration gradient of attractant (chemotaxis). Microbial cells have very efficient chemotaxis systems. Use of two phase aqueous systems should be useful for such separations. For example, an *E. coli* cell that expresses an extracellular gold binding protein domain will bind small particles of gold. The cell will then follow a chemical gradient (e.g., a gradient of the sugar ribose or amino acid aspartate or other chemoattractants) to the collection destination.

VI. Use of High Affinity Binding Proteins for Mineral Exploration.

The present invention also provides a method for determining the source of metal ions in streams, rivers, and drainage basins. In general, streams, rivers, and drainage basins are monitored for the presence of metal ions of interest. Determining the location of metal ions in various locations will allow one to track the course of the ion from its destination in a drainage basin backwards to its source. The approach involves placement of small dialysis sacs, immobilized proteins or similar devices in streams and rivers of a drainage basin for fixed times. The sacs containing proteins that bind metal ions with very high affinities are removed and analyzed for content of mineral ion.

EXAMPLES

Example 1

Field System for Mineral Exploration ("Rock Blot")

A sample (rock) suspected of containing gold was obtained. The surface of the rock was blocked with a 50 µg/ml solution of alkaline phosphatase (P2991) diluted in TTBS (100 mM Tris pH 7.4, 0.5 M NaCl, 0.1% TWEEN® 20 (Polyoxyethylenesorbitan monolaurate)), mixing gently for four hours. The rock was then washed with TTBS buffer, 3×. FITC-GBPAP (Fluoresceinated Gold Binding Protein, 11 µg/ml in PBS) at a concentration of 0.18 µg/ml was added, and incubated for six hours with a rocking mixer. After incubation, the rock was rinsed three times with 6 ml TTBS. The rock was blocked by incubating in dry milk solution in (10% w/v in TTBS) for 30 minutes, followed by three washes with 10 ml TTBS each. Primary antibody (Anti-Fluorescein IgG, Monoclonal, 15 µg/ml in TTBS, Mouse anti-F, ⅟₁₀ Dilution of stock) was added, and the rock was incubated at room temperature overnight with gentle shaking. A VECTASTAIN® kit (Vector Laboratories, Inc., Burlingame, Calif.) was used to bind biotinylated secondary antibody (horse anti-mouse) and avidin-labeled alkaline phosphatase.

Substrate solution was prepared in glass containers by dissolving 5 mg of 4-iodophenol and 20 mg of luminol (5-amino-2,3-dihydro-1,4-pthalazinedione) into 0.5 ml DMSO and adding solution of 0.5 ml 1 M Tris HCl pH 8.5, 21.5 ml ddH$_2$O (double glass distilled H$_2$O), and 2.5 ml 5 M NaCl. 62.5 µl of H$_2$O$_2$ was placed in a separate glass tube.

The detection reaction was initiated in a darkroom. The rock was placed into the into the tris/salt solution face up without shaking. Luminol solution was added to the H$_2$O$_2$ solution, mixed, and them immediately added to the petri dish. After two minutes, the solution were drained away from the rock. The rock surface was covered with plastic wrap and then exposed to Polaroid Type 57 high speed film for 1, 2, 4, 8, 16, 30, and 60 seconds. The film was developed to observe results of the blot.

Example 2

High-Throughput Analysis Protocol (96 Well Plate Assay)

A. Ore samples were puck milled (or powdered by another fashion to the extent of puck milling). Using a 5 mg scoop, samples were transferred into the wells of the 96 well filtration plate (MULTISCREEN® 96-well filtration and assay plate (Millipore, #MAHVN4510). 100 µl of gold binding solution (GBP in Buffer T (50 mM Tris, pH=8, 10 mM CaCl$_2$, 40 mM NaCl, 1% TRITON® X-100 (t-octylphenoxypolyethoxyethanol)), standardized according to EXAMPLE 2B) was added to each well with a multipipettor. The plates were covered with sealing tape (Fisher Scientific #MATAHCL00) and vortexed for 30 mm in a Vortex Mixer with 96 well plate attachment (Fisher Scientific #12-812, 96-attachment is #12-812D). The plate was washed with 200 µl Buffer T fifteen times on a Vacuum Manifold for MULTISCREEN® plates (Millipore Corp.). 100 µl of trypsin (Sigma Chemicals #T8642, TPCK treated) solution (100 µl/ml, in buffer T) was added to each well with a multipipettor. The plate was covered again, and vortexed for 5 mm. The cover was then removed and blotted with a paper towel to remove excess moisture. 25 µl of trypsin inhibitor (Sigma Chemicals #T9003, from soybean) solution (1 mg/ml in buffer T) was added to each well to stop the reaction, and mixed briefly on the lowest setting (uncovered) on the vortex mixer. The entire volume of each well was transferred to a new filter bottom plate (using a 96 well syringe pipettor from Midwest Scientific, St. Louis, Mo.). A standard 96 well plate was placed into the chamber of the vacuum manifold, and the contents of the filter plate were vacuumed through to the top filter plate and into the receiver plate.

For a direct luminescent measurement, five µl of the filtrate is transferred to a 0.5 ml EPPENDORF® tube containing 95 µl of LUMI-PHOS® Plus (luminescent alkaline phosphatase substrate) (Lumigen, Inc., Southfield, Mich. #P-701). The solutions are mixed well and incubated for 1 hour. After 1 hour the tubes are read individually in the luminometer with an adaptor for 0.7 ml Eppendorf tubes. (Turner Designs TD-20/20).

The reaction may also be detected by film. In this case, 95 µl of LUMI-PHOS® Plus is added to each well of an opaque 96 well plate. Five µl of the sample in the standard (clear) 96-well plate is transferred to its corresponding location on the opaque plate and mixed with the vortex mixer on the lowest setting for a few seconds. The plate is incubated at room temperature for one hour and then exposed to Polaroid Type 57 high speed film for several time intervals.

B Standards Assay

To test a new preparation of GBP for efficacy, test several concentrations of GBP with the low gold fire assayed standard (0.02 g/ton) and high gold fire assayed standard (7.59 g/ton) from PD and pick the GBP concentration, that provides the best signal to noise between the two samples. The GBP concentrations were varied between 0.001 and 0.01 mg/ml to start. Optimal protein concentration is determined by maximizing the signal with the high concentration gold sample while keeping the non-specific signal from the low gold concentration ore at a low value.

C. Specificity Assay

The procedure for this assay was the same as that in Example 2A, with the following changes. The Gold Binding Protein Solution is in PKT(50) buffer (10 mM $KH_2PO_4$, 50 mM KCl, 1% Triton X-100, pH≅3.95 (Unadjusted)) instead of Buffer T. The concentration of the GBP was at 200 μg/ml. The samples were covered in sealing tape and vortexed on high for 10 mm. After the vortex step the wells were washed with Tris Calcium Buffer (1 mM $CaCl_2$, 11 mM Tris pH 8.0, pH=8.2 Unadjusted) rather than Buffer T (using the 8-pipettor, 10 washes of 200 μl). Trypsin volume was changed from 100 μl to 200 μl. Concentration remained same at 100 μl/ml. The plate was covered and vortexed for 4 mm. The transfer step was eliminated; and the contents were vacuumed through into the receiver plate. Luminometer incubation volume and time were slightly adjusted. 5 μl of filtrate sample was added to 100 μl of Lumi-Phos Plus and incubation time was shortened to 40 mm.

Example 3

Gold Recovery System (Magnetic Separation)

DYNABEADS® M-280 Tosyl-activated (Dynal A. S., Oslo, Norway, Prod. No. 142.04) (200 μl, 2 mg) are uniform, superparamagnetic, polystyrene beads coated with a polyurethane layer. The polyurethane surface is activated by p-toluenesulphonyl chloride to provide reactive groups for covalent binding of proteins (e.g. antibodies) or other ligands containing primary amino or thiol groups. The beads are washed with 1 ml 0.1 M Na Borate, pH 9.5. 40 μl goat-anti-rabbit IgG (1 μg/μl) were added to 200 μl 0.1 M Na Borate containing 2 mg beads. The beads and the antibody were incubated at room temperature on a rotating shaker overnight. A control reaction contained control beads but no antibody. The beads were washed once with 1 ml Buffer D (PBS+0.1% BSA) then once with 0.5 ml Buffer D. The mixture was blocked overnight in buffer E (0.2 M Tris pH=8.5+0.1% BSA). Wash with 1 ml PKT Buffer (10 mM $KH_2PO_4$, pH 7.0, 10 mM KCl, 1% Triton X-100). Gold beads (20 μl of a 1 mg/ml suspension, 1.5–3.0 micron, Aldrich Chemical Co. #32658-5), were mixed with 30 μl PKT and 50 μl 1.11 mg/ml GBP in 50 mM Tris pH=8.0, (final concentration is 0.5×PKT (10 mm KCl)) and incubated overnight at room temperature on a rotating shaker. The overnight incubation ensures maximum bead coverage. The beads were washed 4 times with 1 ml PKT buffer.

Anti Alkaline Phosphatase Antibody (polyclonal, Harlan Sera-Lab #ENZ-020) (1.2 mg in 120 μl PKT) was added to the GBP-Au bead solution and incubated with gentle mixing for four hours. After incubation, the beads were washed twice with 1 ml PKT buffer. Twenty μg of the resulting beads (Au plus GBP plus anti AP) were mixed with the Dynabeads and incubated with rotation for one hour. After mixing the solutions, a magnetic field is applied with a Dynal MPC-P-12 Magnetic particle concentrator for 0.5 ml Eppendorf Tubes (Prod. No: 120.10). Gold beads without GBP attached were used as a control.

Example 4

Gold Flotation

Colloidal gold (1 ml, Sigma, #G1402, 5 nM,) was added to three 1.5 ml Eppendorf tube and the tubes centrifuged for fifteen minutes in a microcentrifuge at 12,000 rpm. The supernatant was removed and one tube of the colloid was resuspended in a solution of GBP (0.333 mg/ml in 50 mM Tris pH=8.0). Two other control tubes were resuspended in $ddH_2O$ only. The tubes were incubated on a rotating mixer overnight to allow binding to occur. The tubes were centrifuged for fifteen minutes in a microcentrifuge at 12,000 rpm to remove excess GBP, and the colloid was resuspended in 1 ml phosphate buffer (pH=6)(43.85 ml 0.2 M $NaH_2PO_4$, 6.15 ml 0.2 M $Na_2HPO_4$) three to four times. Valeric anhydride (2 μl, Sigma #V-6127) was added to the tube with GBP and to one of the control tubes. Mineral oil (100 μl) was added to each tube and the tubes vortexed for 2–3 minutes. The tubes were allowed to settle and the oil and water to separate.

Example 5

GBP Binding Using 1.5–3.0 Micron Spherical Au Particles

A. Preparation of Gold Beads. 10 mg of 1.5–3.0 micron Au powder (Aldrich Chemical #32.658-5) was suspended in 1 ml of 10% Hydrofluoric acid (HF) and incubated on a rotating mixer at room temperature overnight (to clean any organic debris from the beads). The beads were washed by spinning at 10,000 RPM in a microfuge for 1 minute. The supernatant was decanted and the gold beads resuspended in 1 ml PKT(50) at pH=7.0. The wash procedure was repeated four times, with the beads in a final volume of 1 ml. The beads were vortexed vigorously and 10 μl of this suspension was immediately pipetted to another 1.5 ml Eppendorf tube, yielding 100 μg of Au beads per tube.

B. Gold bead assay. 500 μl of GBP solution at 10 μg/ml in PKT(50) buffer, pH=7.0 was added to the gold containing tube and incubated for 30 minutes at room temperature on a rotating mixer (the tube was rotated end over end because the beads settle rapidly). After 30 minutes, the beads were washed three times as described above in EXAMPLE 3A.

C. Trypsinization. The final pellet was resuspended in 200 μl trypsin solution (10 μg/ml trypsin (Sigma Chemicals #T8642, TPCK treated) in trypsin buffer (10 mM Tris pH=8.0, 10 mM $CaCl_2$)). After five minutes on the mixer, the Au beads were spun down again. The supernatant was assayed for AP activity by adding 5 μl of the supernatant to 100 μl Lumi-Phos® Plus and then reading in the luminometer after a 30 minute incubation.

Example 6

GBP Binding Using Gold-Coated Slides

This procedure is an improvement on the Au bead assay for determination of GBP binding ability. Using a gold-coated slide in place of the Au beads greatly reduces the variability that was previously observed, most likely due to a much more uniform and reproducible surface.

A. PNPP assay. For determination of GBP-AP alkaline phosphatase activity, 10 μl of GBP solution was added to 1 ml of the PNPP (p-Nitrophenyl Phosphate, Sigma #104-0, 52 mg in 50 ml 50 mM Tris pH 8.0). The change in absorbance was measured at an O.D. of 600 nM. Slope was multiplied by 100 to yield PNPP units per ml.

B. Gold slide assay. A glass slide (15×4 mm) was incubated in a 1.5 ml Eppendorf tube containing 1 ml of GBP solution. The concentration of GBP was around 10 µg/ml in PKT(50) buffer. The incubation was at room temperature on a shaking incubator for 30 minutes. The slide was removed and rinsed with ddH$_2$O. The slide was placed into a 1.5 ml Eppendorf tube containing 1 ml Lumi-Phos® Plus and incubated on shaking incubator for 30 min. 100–500 µl samples were analyzed in a Turner TD 20—20 Luminometer.

What is claimed is:

1. A method for detecting gold in at least one ore sample, comprising:
   a) obtaining an ore sample suspected of containing gold;
   b) contacting a surface of said ore sample with a gold-specific protein; and
   c) detecting the presence of the gold-specific protein on said surface of said ore sample;
   whereby gold is detected.

2. The method of claim 1, further comprising quantitating the gold that is detected.

3. A method for detecting gold in at least one ore sample, comprising:
   a) obtaining an ore sample suspected of containing gold;
   b) contacting a surface of said ore sample with a gold-specific protein;
   c) contacting said surface with a proteolytic agent to proteolyze said gold-specific protein into a proteolytic fragment; and
   d) detecting said proteolytic fragment;
   whereby gold is detected.

4. The method of claim 3, wherein the gold-specific protein is GBP.

5. The method of claim 3, wherein the proteolytic agent is trypsin.

6. The method of claim 3, wherein said proteolytic fragment is the alkaline phosphatase domain of GBP.

7. The method of claim 3, wherein the method is performed in a multiwell plate.

8. The method of claim 7, wherein the detection comprises luminescent detection.

9. The method of claim 8, wherein the detection comprises exposure of the multiwell plate to light-sensitive film.

10. The method of claim 3, wherein the detection is quantitative.

11. The method of claim 8, wherein the detection is quantitative.

* * * * *